United States Patent [19]

Ritson et al.

[11] Patent Number: 5,041,088
[45] Date of Patent: Aug. 20, 1991

[54] MULTIPLE CHAMBER AUTOMATIC INJECTOR

[75] Inventors: Geoffrey Ritson, Turnbridge Wells; John G. Wilmot, Leybourne, both of England

[73] Assignee: Medimech International Ltd., Wembley, England

[21] Appl. No.: 396,325

[22] Filed: Aug. 21, 1989

[30] Foreign Application Priority Data

Aug. 23, 1988 [GB] United Kingdom ............... 8819977

[51] Int. Cl.⁵ .............................................. A61M 5/00
[52] U.S. Cl. ...................... 604/88; 604/82; 604/135; 604/138; 604/191; 604/206
[58] Field of Search ............... 604/68, 71, 82, 87–92, 604/111, 130, 134–135, 138, 157, 181, 187, 191, 136, 194–196, 200, 205–206

[56] References Cited

U.S. PATENT DOCUMENTS

| 1,943,120 | 1/1934 | Kabnick | 604/87 |
| 2,688,966 | 9/1954 | Huber | 604/90 |
| 4,059,109 | 11/1977 | Tischlinger | 604/88 |
| 4,316,463 | 2/1982 | Schmitz et al. | 604/135 |
| 4,484,910 | 11/1984 | Sarnoff et al. | 604/134 X |
| 4,643,721 | 2/1987 | Brunet | 604/191 |
| 4,822,340 | 4/1989 | Kamstra | 604/89 X |

FOREIGN PATENT DOCUMENTS 1094932 12/1960 Australia .................. 604/134

Primary Examiner—C. Fred Rosenbaum
Assistant Examiner—Corrine Maglione
Attorney, Agent, or Firm—Renner, Kenner, Greive, Bobak, Taylor & Weber

[57] ABSTRACT

An automatic injector is provided having at least two chambers containing different ingredients of a medicament separated by an impermeable membrane. A lance is movable independently of a plunger to cut or pierce the membrane before a spring-loaded drive member for the plunger is released to drive a needle out of the body of the injector and discharge the medicament through the needle. A removable safety clip is provided for preventing movement of an actuating cap into an operative position for advancing the lance, and release of the drive member is preventable by a removable safety pin until the injector is to be used.

15 Claims, 2 Drawing Sheets

MULTIPLE CHAMBER AUTOMATIC INJECTOR

This invention relates to automatic injectors of the kind comprising a body which contains a charge of medicament, a needle held in a sheathed position within the body, releasable drive means which when released drives the needle from its sheathed position to an unsheathed position projecting from the body, and expulsion means for discharging the medicament through the needle. Automatic injectors of this kind will hereinafter be referred to as of the kind set forth.

Automatic injectors of the kind set forth have been developed primarily for use by persons who have to administer an injection into their own body at an instance which is not known beforehand. These persons include soldiers who, when wounded, accidentally injured or exposed to battle gas, such as nerve gas, rapidly need to self-inject a medicament into their own body. Such injectors, of course, can be used by one person to administer an injection into another person or animal and therefore have secondary uses in hospitals, emergencies and for veterinary purposes.

Automatic syringes which have a single chamber for the medicament in the form of a pre-mixed fluid are well-known and one such injector is disclosed in U.S. Pat. No. 2,832,339. Single chamber syringes, however, suffer from the disadvantage that the type of medicaments that can be kept in them is limited. Many pre-mixed medicaments have a limited storage life after which the medicament is unsuitable for injection. Moreover, it is necessary to prepare some medicaments from different ingredients, for instance, a powder and a liquid or two incompatible liquids, immediately before the medicament is to be injected. Single chamber syringes, therefore, cannot be used for containing medicaments such as military vaccines, nerve gas antidotes and other non military medicaments consisting of two or more ingredients which cannot be stored in contact with each other for any significant length of time.

U.S. Pat. No. 3,572,336 discloses an automatic syringe which can be used to administer different liquids simultaneously to a patent from a plurality of chambers arranged side-by-side within a common housing through either a plurality of needles or a single needle. In use the or each needle is injected into the patient before movement of a plunger within each chamber causes a membrane disposed between each chamber and the needle or needles to burst under hydrostatic pressure allowing the liquids to pass through the needle or needles and into the patient. However, this device utilising chambers side-by-side, is bulky and cannot be used when one or more of the ingredients of the medicament to be injected is of powdered form.

There have also been attempts to provide automatic injectors in which different ingredients of the medicament are stored in separate chambers and a passage between the chambers is opened to allow the ingredients to mix before the medicament is injected. WO 86/06967 discloses one such automatic injector which has two chambers side-by-side in a common housing interconnected by a conduit in the partition between the chambers that opens when a plug or stopper moves past the conduit.

EP-A-0 072 057 discloses another type of multi-chamber automatic syringe in which different injection liquids are separated by a plug or stopper which is movable forwardly in the syringe into a position in which a by-pass around the plug or stopper allows the liquids to mix before they are expelled from the syringe. Such multi-chamber automatic injectors have not been greatly successful because it has been difficult to find a suitable material for the plug or stopper which is not only impermeable and will not be adversely affected by highly reactive ingredients such as those of nerve gas antidotes, but which also allows the plug or stopper to slide easily within the syringe whilst providing an effective seal between the chamber or each side of the plug or stopper.

It is an aim of the present invention to provide a multi-chamber automatic injector of the kind set forth in which at least two different ingredients of a medicament can be stored separately, which enables the different ingredients to be mixed if necessary before the medicament is automatically injected, and which does not suffer from some of the disadvantages associated with previously proposed automatic multi-chamber syringes.

According to the present invention there is provided an automatic injector of the kind set forth incorporating at least two chambers for containing different ingredients of a medicament, in which adjacent chambers of the injector are separated by an impermeable membrane, and cutting or piercing means is provided which is movable within the body to cut or rupture the membrane before the drive means is released.

The provision of the cutting or piercing means enables a controlled rupture of the impermeable membrane to take place. It also allows the different ingredients of the medicament to be mixed thoroughly, if necessary, before they are injected. Thorough mixing of the ingredients prior to injection is particularly essential when one of the ingredients is in powdered form.

Preferably, the body of the injector is of elongate form with the chambers for the different ingredients arranged axially in the body, and the or each impermeable membrane which separates adjacent chambers extends transversely across the body. Conveniently, a first chamber for one ingredient is arranged to contain the needle in its sheathed position and a second chamber for another ingredient is arranged to contain the cutting or piercing means. This arrangement is advantageous in that the overall length and diameter of the body of the syringe is not increased very significantly than would be expected in a multi-chamber syringe when compared with single chamber automatic syringes.

In a preferred arrangement the body of the automatic injector has a substantially cylindrical bore containing a tubular cartridge which lines the bore and has at least two axially spaced cylindrical chambers for different ingredients of a medicament, adjacent chambers being separated by an impermeable rupturable membrane extending across the cartridge at an intermediate point along the length of the cartridge.

The cutting or piercing means may comprise a lance which is arranged to extend and be slidable through a plunger which constitutes the expulsion means and seals off the end of the second chamber opposite the membrane, the plunger in turn being slidable within the cartridge to discharge the medicament through the needle when the drive means is released.

The cartridge is preferably formed from a chemically inert, impermeable, low-friction plastics material. The membrane may be formed from the same material as the cartridge or from a different material or materials. The arrangement is preferably such that, after rupture, the membrane does not obstruct movement of the plunger and, where mixing of the ingredients is necessary, the ruptured membrane does not interfere with said mixing or with the discharge of medicament through the needle. Desirably, the membrane is thin enough so that if it is squeezed between the wall of the cartridge and the plunger after it has been ruptured, the seal between the plunger and the cartridge wall is maintained. The membrane however, is preferably highly impermeable, tough and has sufficient mechanical strength so as not to rupture accidentally during transportation.

The releasable drive means may comprise a spring-loaded drive member engageable with the plunger and having latching means for holding a spring in compression, the drive member being urged by the spring to advance the plunger when the latching means is released.

Conveniently, after the lance has cut or ruptured the membrane it is arranged to engage with the needle and is movable with the plunger to force the needle out of the body of the injector into its unsheathed position, and when the needle has reached its fully extended position the plunger is preferably arranged to continue its movement within the liner to expel the contents of the first and second chambers through the needle.

Preferably, there is provided means for advancing the lance to cut or rupture the membrane which is movable independently of the drive member. In a preferred embodiment the drive member comprises a tubular collet and the lance is advanced by an element such as a drive pin movable within the tubular collet.

The releasable drive means and the means for advancing the cutting or piercing means may be actuated by a common actuating member which is initially movable to advance the cutting or piercing means, release of the drive means being effected by further movement of the actuating member. Alternatively, separate actuating members may be provided for advancing the cutting or piercing means and for releasing the drive means.

In order to prevent accidental actuation of the automatic injector, removable safety elements may be provided both for preventing advancement of the cutting or piercing means and for preventing release of the drive means until it is desired to use the automatic injector. The removable safety elements may be separate with tamper evident means being provided for indicating removal of the first safety element, or optionally they may be linked together in such a manner that the safety element preventing release of the drive means cannot be removed until the safety element preventing advancement of the cutting or piercing means has been removed.

An embodiment of the present invention will now be described, by way of example only, with reference to the accompanying drawings in which.

Figure 1:
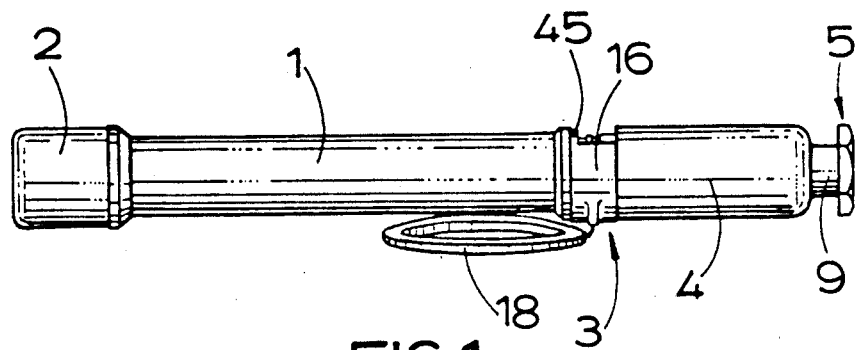
FIG. 1 is a side view of an automatic hypodermic injector in accordance with the invention.

The automatic hypodermic injector shown in the drawings comprises an elongate, substantially cylindrical body 1 with a closed end cap 2 at one end and a removable safety clip 3, an actuating cap 4 and a safety pin 5 at its opposite end.

The closed end cap 2 is permanently attached to said one end of the cylindrical body 1 by means of a snap engagement and contains a sealing bush 6 which seals the contents of the injector at that end from the atmosphere. The end wall 7 of the end cap 2 has a portion 8 of reduced thickness at its center.

The actuating cap 4 has a first annular portion 11 which surrounds said opposite end of the body 1 and a second annular portion 9 of reduced diameter which terminates in an end wall in which a central bore 10 is provided. The first annular portion 11 has a radially inturned flange 12 received by means of a snap engagement in a recess 13 defined between two annular ridges 14 and 15 on the outer surface of said opposite end of the body 1. The removable safety clip 3 is in the form of a wide band 16 extending around approximately three quarters of the circumference of the body 1 and a narrow tamper evident tag 45 extending around the remaining part of the body. The band 16 is disposed between a shoulder 17 on the body 1 and the end of the first annular portion 11 of the actuating cap 4 and prevents movement of the actuating cap towards the shoulder 17. The band 16 of the safety clip 3 is connected to a pull ring 18 which facilitates removal of the safety clip 3. Preferably, the pull ring 18 is flexible and can fold against the body 1 in storage. Breakage of the tamper evident tag 45 before legitimate use of the injector is required indicates that the injector has been tampered with or partially used.

The safety pin 5 has an enlarged head 19 at one end of an intermediate portion 20 disposed within the bore 10 in the second annular portion 9 of the actuating cap 4 and a cylindrical shank 21 of reduced diameter which extends into the actuating cap from the other end of the intermediate portion 20. In an optional feature the safety pin 5 may be linked to the safety clip 3 by a tie so that the safety pin 5 cannot be removed until the safety clip 3 has been removed.

The body 1 of the injector has a stepped cylindrical bore having bore portions 23 and 24 of greater and lesser diameter which meet at a shoulder 25 roughly half way along the bore.

The bore portion 23 of greater internal diameter is nearest the end cap 2 and is lined by a tubular cartridge or liner 26 in abutment with the shoulder 25. The liner 26 is preferably made from a chemically inactive, impermeable, low-friction plastics material such as FEP, a fluoro-co-polymer. The inner wall of the tubular liner 26 defines first and second cylindrical chambers 27 and 28 which are separated by a thin, tough, impermeable membrane 29 bonded around its circumference to the wall of the liner 26 at an intermediate point along its length. If the membrane 29 is welded to the liner 26 there may be an annular weld flash on the outer surface of the liner 26. The bore portion 23 in this case may have an additional shoulder indicated at 46 to accommodate such a weld flash.

Figure 3:
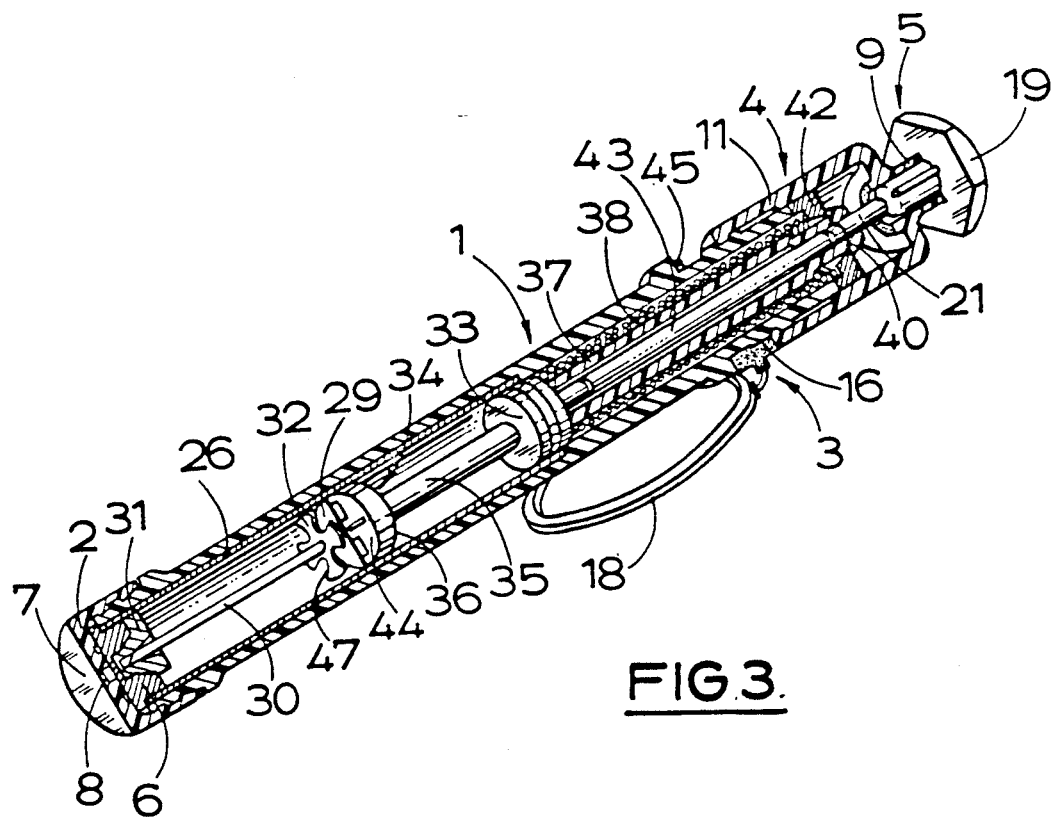
FIG. 3 is a cut-away perspective view showing the components within the injector of FIGS. 1 and 2.

The first chamber 27 nearest the end cap 2 contains a hollow hypodermic needle 30 surrounded at its pointed end by a generally frusto-conical needle guide 31 which fits into a complementary part of the sealing bush 6. The end of the needle 30 remote from its point is connected to a surrounding needle disc 32 which is spaced a short distance away from the impermeable membrane 29. The disc 32 is preferably formed with openings or recesses 47 in its outer edge. In FIG. 3 it is shown having a shape similar to that of a Maltese Cross.

The second chamber 28 is bounded at one end by the membrane 29 and at its opposite end by a plunger 33 slidably received within the liner 26. The second chamber 28 contains a lance 34 having a cylindrical stem 35 which extends at one end through the plunger 33 and which carries on its other end a cutter 36 spaced a short distance away from the membrane 29.

The bore portion 24 of lesser internal diameter contains releasable drive means for the plunger 33 in the form of a tubular collet 37 surrounded by a helical spring 38. The collet 37 at one end has an enlarged head 39 which engages with the plunger 33 and at its other end has a latching means in the form of a frusto-conical portion divided by one or more slots into barbs 40 which extend through a central opening 41 in an annular collar or latch ring 42 at the end of the body 1 onto which the actuating cap 4 fits. If the collet 37 is formed from a plastics material one slot may be sufficient, but a metal collet preferably has four slots in its frusto-conical portion. The barbs 40 of the frusto-conical portion engage with the outer face of the collar 42 and the spring 38 is held in compression between the inner face of the collar 42 and the head 39 of the collet 37.

Figure 2:
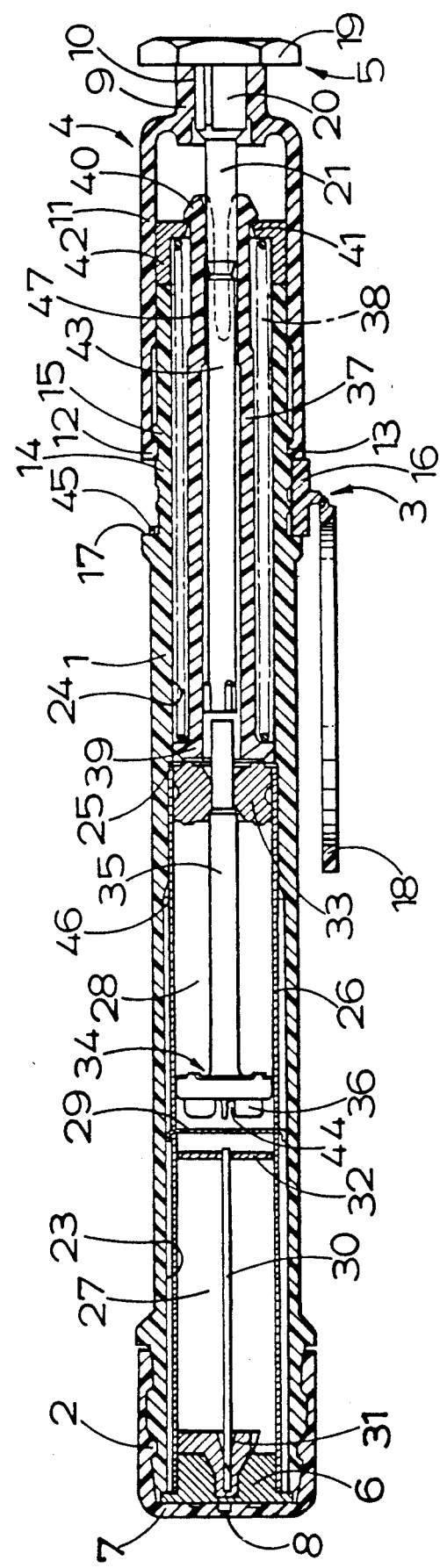
FIG. 2 is an enlarged longitudinal section through the injector of FIG. 1.

Within the tubular collet 37 there is a drive pin 43 which engages at one end with the lance 34 and at its opposite end with the shank 21 of the safety pin 5 which extends partly within the divided frusto-conical portion 40 of the collet 37. In a modified construction, not shown, the drive pin 43 and safety pin 5 may comprise a single component. With a separate drive pin 43 an interference fit may be provided between the drive pin 43 and the collet 37. This allows the drive pin 43 to slide within the collet bore with negligible friction, but will prevent the drive pin 43 from falling out of the collet 37 during assembly and also will stop the drive pin moving into a position where it may prevent firing by preventing the collet barbs from collapsing fully. FIG. 2 shows the interference fit provided at 47 between the collet 37 and the end of the drive pin 43 adjacent to the shank 21 of the safety pin 5. Preferably, however, two or more ribs are provided at the opposite end of the drive pin 43 with a slot or slots up the end of the drive pin to provide a spring-type cantilever interference fit.

In use the first and second chambers 27 and 28 of the injector are filled with different ingredients of a medicament to be injected. For instance, the second chamber 28 may contain a medicament in powdered form and the first chamber 27 a diluent for the powder, or vice versa. Alternatively, the chambers may contain different liquid ingredients of a medicament that are incompatible if stored together for any significant length of time. The pre-filled automatic injector may be carried by a user in the condition shown in the drawings and preferably contained within a close fitting flexible plastics sleeve (not shown) which has appropriate labelling, attachment means, e.g. a button hole, and is designed to act as a casualty marker tag after use. When the user needs to self-inject the medicament into his/her body he/she follows the procedure described below.

The user pulls the ring 18 of the safety clip 3 to remove the band 16 from the body of the injector breaking the tamper evident tag 45. Then, by pressing down on the head 19 of the safety pin 5 the flange 12 of the annular portion of the actuating cap 4 moves over the annular ridge 14 and the drive pin 43 moves within the collet 37 and advances the lance 34 which ruptures the membrane 29, allowing the ingredients in the chambers 27 and 28 to mix.

It will be appreciated that the membrane may be ruptured in a variety of ways. As shown in FIGS. 2 and 3 the cutter 36 on the lance 34 may be arranged to cut a plurality of radial slits (e.g. four) in the membrane 29 allowing the cut sectors to be pushed by the head of the lance 34 against the wall of the liner 26 allowing free passage of the plunger through the membrane region. A central recess 44 in the cutter 36 is designed to allow fluid to flow down the end of the needle tube. Alternatively, the cutter 36 on the lance may be arranged to cut the periphery of the membrane 29 which can then fold up into the central recess 44 in the lance so that it does not obstruct the flow of liquid ingredients from the second chamber 28 into the first chamber 27. The lance, however, may take different forms and the membrane 29 may be ruptured by a piercing action instead of a cutting action.

After the ingredients of the medicament within the injector have been thoroughly mixed together, the user removes safety pin 5, places the end cap 2 on an appropriate part of his/her body, his/her thigh for example, and self-injects the medicament into his/her body by pressing on the actuating cap 4.

Removal of the shank 21 of the safety pin 5 from within the divided frusto-conical portion of the collet 37 allows the barbs 40 to collapse inwardly when the part of the end wall 9 that defines the aperture 10 engages the barbs 40. When the barbs 40 of the collet 37 collapse inwardly through the collar 42, the compressed spring 38 is released and drives the collet 37, plunger 33 and lance 34 forwards in the body.

When the collet 37 starts moving the plunger 33 drives the lance 34 down onto the needle disc 32, the needle 30 then pierces the needle guide 31, sealing bush 6 and portion 8 of the end cap 2 and continues moving into the body of the user until the needle disc 32 is touching the needle guide 31. During the movement of the needle 30 the medicament will be pumped out of the chambers 27 and 28 through the needle 30 by the plunger 33. The medicament will normally enter the needle tube through a hole in the end of the needle opposite its pointed end. There may, however, also be provided a slot in the side of the needle tube, just below the needle disc so that if the end of the needle tube is blocked by a piece of the cut membrane there is a second path for the fluid to flow down the needle tube. When the needle stops moving the plunger 33 will continue moving and will slide over the top of the cylindrical stem 35 of the lance 34. This will continue until the plunger 33 is pushed to the bottom of the lance 34 which will be on top of the needle disc 32 therefore expelling the medicament from both chambers 27 and 28 of liner 26. At the end of the operation of the automatic injector the needle 30 will be fully projecting from the end cap 2, the cutter 36 of the lance 34 will be on top of the needle disc 32, the plunger 33 will be on top of the cutter 36, the collet 37 will be on top of the plunger 33, the spring 38 will be fully extended, the drive pin 43 should remain in the collet 37, the safety pin 5 and clip 3 will be removed with the tamper evident tag 45 broken indicating that the device has been used and the actuating cap 4 may be pushed fully down on top of the body 1 or returned to its original position by the spring 38.

It will be appreciated that the multi-chamber automatic injector of the present invention is simple to operate and effectively stores the different ingredients of the medicament in separate chambers with minimal risk of the ingredients being mixed together until the user is ready to self-inject the medicament into his/her body. This substantially prolongs the storage life of the injector and also greatly increases the number of different medicaments which can be injected using the automatic injector.

I claim:

1. An automatic injector comprising a body incorporating at least two chambers containing different ingredients of a medicament, said chambers being adjacent one another and separated by a thin impermeable membrane, a needle held in a sheathed position within said body, releasable drive means within said body which when released drives said needle from said sheathed position into an unsheathed position projecting from said body, expulsion means within said body for discharging the medicament through said needle, and a cutting or piercing means which is movable within said body from a first position in which it is separated from said membrane to a second position where it is forcibly in contact with said membrane so as to cut or pierce said membrane before said drive means is released.

2. An automatic injector according to claim 1, wherein said chambers for the different ingredients of the medicament are arranged axially in said body of the injector.

3. An automatic injector according to claim 2, wherein a first one of said chambers is arranged to contain said needle in said sheathed position and a second one of said chambers is arranged to contain said cutting or piercing means.

4. An automatic injector according to claim 3, wherein the automatic injector has a substantially cylindrical bore within said body lined by a tubular cartridge which defines said adjacent axially spaced chambers, and said impermeable membrane separating said chambers extends transversely across said cartridge at an intermediate point along the length of said cartridge.

5. An automatic injector according to claim 4, wherein said tubular cartridge is formed from a chemically inert, impermeable, low-friction plastics material.

6. An automatic injector according to claim 1, wherein said cutting or piercing means comprises a lance arranged to extend through a plunger and be slidable relative to said plunger which constitutes said expulsion means for discharging the medicament through the needle.

7. An automatic injector according to claim 6, wherein said releasable drive means comprises a spring-loaded drive member engageable with said plunger and latching means associated with said releasable drive means, said latching means serving for holding a spring in compression, said drive means being urged by said spring to advance said plunger when said latching means is released.

8. An automatic injector according to claim 7, wherein said needle carries a disc and said lance is engageable with said disc after said lance has cut or pierced said membrane, said lance being subsequently movable with or by said plunger to force said needle out of said body of the injector into said unsheathed position, said plunger being arranged to continue its movement when said needle is in said unsheathed position to expel said medicament from said chambers through said needle.

9. An automatic injector according to claim 8, including means for advancing said lance which is movable independently of said drive member of said releasable drive means.

10. An automatic injector according to claim 9, wherein said drive member of said releasable drive means comprises a tubular collet engageable with said plunger, and said means for advancing said lance comprises a drive pin movable within said collet.

11. An automatic injector according to claim 1, wherein a first removable safety element prevents movement of said cutting or piercing means and a second removable safety element prevents release of said drive means.

12. An automatic injector according to claim 11, wherein an end cap is provided on said body, said end cap being movable relative to said body with said second safety element when said first safety element is removed to advance said cutting or piercing means and said end cap being subsequently movable relative to said body to effect release of said releasable drive means and advance said expulsion means.

13. An automatic injector according to claim 12, wherein a tamper evident means is provided for indicating removal of said first removable safety element.

14. An automatic injector comprising a body incorporating at least two chambers, each containing different ingredients of a medicament, such chambers being adjacent to one another and separated by a thin impermeable membrane, a needle held in a sheathed position within said body, releasable drive means within said body which, when released, drives said needle from said sheathed position into an unsheathed position projecting from said body, a plunger within said body constituting expulsion means for discharging the medicament through said needle, cutting or piercing means comprising a lance arranged to extend through, and be slidable relative to, said plunger, said releasable drive means comprising a spring-loaded drive member engageable with said plunger and latching means associated with said releasable drive means, a spring held in compression by said latching means, said drive member being urged by said spring to advance said plunger when said latching means is released, and means for advancing said lance which is movable independently of said drive member.

15. An automatic injector according to claim 14, wherein said drive member of said releasable drive means comprises a tubular collet engageable with said plunger, and said means for advancing said lance comprises a drive pin movable within said collet.

* * * * *